(12) United States Patent (10) Patent No.: US 12,629,294 B2

Ito (45) Date of Patent: May 19, 2026

(54) ABSORBENT ARTICLE

(71) Applicant: DAIO PAPER CORPORATION, Ehime (JP)

(72) Inventor: Rina Ito, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 358 days.

(21) Appl. No.: 18/249,404

(22) PCT Filed: Mar. 23, 2022

(86) PCT No.: PCT/JP2022/013545
§ 371 (c)(1),
(2) Date: Apr. 18, 2023

(87) PCT Pub. No.: WO2023/053523
PCT Pub. Date: Apr. 6, 2023

(65) Prior Publication Data
US 2023/0355450 A1 Nov. 9, 2023

(30) Foreign Application Priority Data
Sep. 28, 2021 (JP) ................................. 2021-158364

(51) Int. Cl.
*A61F 13/47* (2006.01)
*A61F 13/514* (2006.01)
*A61F 13/56* (2006.01)

(52) U.S. Cl.
CPC ...... *A61F 13/5611* (2013.01); *A61F 13/4704* (2013.01); *A61F 13/51474* (2013.01)

(58) Field of Classification Search
CPC ............... A61F 13/4704; A61F 13/472; A61F 13/51104; A61F 13/51108; A61F 13/5605;
(Continued)

(56) References Cited

U.S. PATENT DOCUMENTS 4,690,680 A * 9/1987 Higgins .............. A61F 13/5611
604/386
5,674,341 A * 10/1997 Ng ...................... A61F 13/4756
604/366
(Continued)

FOREIGN PATENT DOCUMENTS

JP 2006-247088 9/2006
JP 2006-296974 11/2006
(Continued)

OTHER PUBLICATIONS

International Search Report for PCT/JP2022/013545 mailed on May 31, 2022.
(Continued)

*Primary Examiner* — Catharine L Anderson
(74) *Attorney, Agent, or Firm* — IPUSA, PLLC

(57) ABSTRACT

An absorber has at least one continuous groove and a back sheet provided on a non-skin side with a plurality of adhesive displacement stoppers, for fixing the absorbent article to underwear. One continuous groove has a shape having two or more portions protruding toward a front of the continuous groove and/or having two or more portions protruding toward a rear of the continuous groove. The continuous groove includes a groove portion, where an imaginary region overlaps the continuous groove, the groove portion having an area of 3% or greater of the region, the groove portion not overlapping a centerline extending in the front-rear direction in plan view. The displacement stopper overlaps an entirety of the continuous groove in the width direction and an entirety of the groove portion in the front-rear direction, or does not overlap the groove portion, in plan view.

5 Claims, 6 Drawing Sheets

(58) Field of Classification Search
CPC ... A61F 13/5611; A61F 13/533; A61F 13/546
See application file for complete search history.

(56) References Cited

U.S. PATENT DOCUMENTS

| | | | | |
|---|---|---|---|---|
| 5,807,365 A * | 9/1998 | Luceri | | A61F 13/533 |
| | | | | 604/370 |
| 7,078,583 B2 * | 7/2006 | Kudo | | A61F 13/47227 |
| | | | | 604/385.01 |
| 8,859,842 B2 * | 10/2014 | Wilson | | A61F 13/533 |
| | | | | 604/385.101 |
| 8,912,384 B2 * | 12/2014 | Suzuki | | A61F 13/4704 |
| | | | | 604/379 |
| 2007/0282287 A1 * | 12/2007 | Noda | | A61F 13/5611 |
| | | | | 604/385.01 |
| 2010/0191210 A1 * | 7/2010 | Hayashi | | A61F 13/5611 |
| | | | | 604/389 |
| 2012/0103504 A1 | 5/2012 | Deng et al. | | |

FOREIGN PATENT DOCUMENTS

| | | |
|---|---|---|
| JP | 2007-167453 | 7/2007 |
| JP | 2007-236649 | 9/2007 |
| JP | 2012-075553 | 4/2012 |
| JP | 2013-248309 | 12/2013 |
| JP | 2014-012210 | 1/2014 |
| JP | 2017-221265 | 12/2017 |
| JP | 2020-039508 | 3/2020 |
| JP | 2021-020009 | 2/2021 |

OTHER PUBLICATIONS

Japanese Office Action for 2021-158364 mailed on Oct. 1, 2024.
Japanese Office Action for 2021-158364 mailed on Apr. 16, 2024.

* cited by examiner

<CONVENTIONAL TECHNIQUE>

ABSORBENT ARTICLE

TECHNICAL FIELD

The present invention relates to an absorbent article.

BACKGROUND ART

As an absorbent article such as a sanitary napkin, a panty liner, or an incontinence pad, a configuration including a skin-side permeable top sheet, a non-skin-side impermeable back sheet, and an absorber disposed between the both sheets is known. Further, the above-described absorbent article is generally provided on the non-skin side (the side opposite to the side facing the skin) with a displacement stopper for preventing the absorbent article from being displaced from underwear when worn.

The displacement stopper of the absorbent article is often formed by applying an adhesive. In addition, various forms of arrangement for the displacement stopper are known, and an absorbent article in which an adhesive is applied in multiple stripes extending in the width direction of the absorbent article is also known (for example, Patent Document 1).

RELATED ART DOCUMENT

[Patent Document]

[Patent Document 1] Japanese Patent Application Laid-Open No. 2006-296974

SUMMARY OF THE INVENTION

Problem to be Solved by the Invention

Incidentally, many absorbent articles have compressed grooves formed by locally compressing the top sheet and the absorber for promoting appropriate deformation suitable for the shape of the body when worn. In this case, even if the groove is formed by pressing on the skin side, the groove corresponding to the pressed portion on the skin side is more or less formed on the non-skin side (back sheet side) of the absorbent article.

When the above-described displacement stopper is applied across the groove formed on the non-skin side, air bubbles enter between the back sheet and the displacement stopper to form a gap, and a portion where the back sheet and the displacement stopper are not in contact with each other may be formed. If there is a non-contact portion therebetween, the adhesive force between the displacement stopper and the underwear becomes larger than the adhesive force between the displacement stopper and the back sheet. For this reason, when the absorbent article attached to the underwear is removed, the displacement stopper may come off from the back sheet and remain on the underwear. In view of the fact that many of users pull the absorbent article off from the front side to the rear side, such a residual displacement stopper is likely to occur in a place where a groove is formed, the groove containing a large amount of component extending across the front-rear direction which is the pulling direction to remove the absorbent article from the underwear, that is, a groove containing a large area extending in the width direction. Further, when displacement stoppers are formed in multiple stripe shapes extending in the width direction of the absorbent article as described in Patent Document 1, the displacement stopper is likely to be torn in the front-rear direction, and the displacement stopper is more likely to remain on the underwear.

In view of the above, an object of one aspect of the present disclosure is to prevent the adhesive displacement stopper from remaining on the underwear when the absorbent article is removed from the underwear.

Means for Solving the Problem

According to one aspect of the present invention, there is provided an absorbent article including a skin-side permeable top sheet, a non-skin-side impermeable back sheet, and an absorber disposed between the top sheet and the back sheet, the absorbent article having a front-rear direction corresponding to a front-rear direction of a body of a wearer and a width direction orthogonal to the front-rear direction, wherein the absorber has at least one continuous groove recessed from a non-skin side to a skin side, wherein the back sheet is provided on a non-skin side with a plurality of adhesive displacement stoppers, each having a length in the width direction longer than a length in the front-rear direction, at intervals in the front-rear direction, for fixing the absorbent article to underwear, wherein the continuous groove has a shape having two or more portions protruding toward a front of the continuous groove and/or having two or more portions protruding toward a rear of the continuous groove, wherein the continuous groove includes a groove portion, where an imaginary region overlaps the continuous groove, the groove portion having an area of 3% or greater of the imaginary region, the groove portion not overlapping a centerline extending in the front-rear direction in plan view, the imaginary region having both a unit length in the front-rear direction and a same length in the width direction as the absorber, and wherein the displacement stopper overlaps an entirety of the continuous groove in the width direction and an entirety of the groove portion in the front-rear direction, or does not overlap the groove portion, in plan view.

Effects of the Invention

According to one aspect of the present disclosure, it is possible to prevent an adhesive displacement stopper from remaining on underwear when an absorbent article is removed from the underwear.

BRIEF DESCRIPTION OF THE DRAWINGS

FIG. 6 is a partially enlarged view of FIG. 2 for explaining a predetermined groove portion.

EMBODIMENTS FOR CARRYING OUT THE INVENTION

Figure 1:
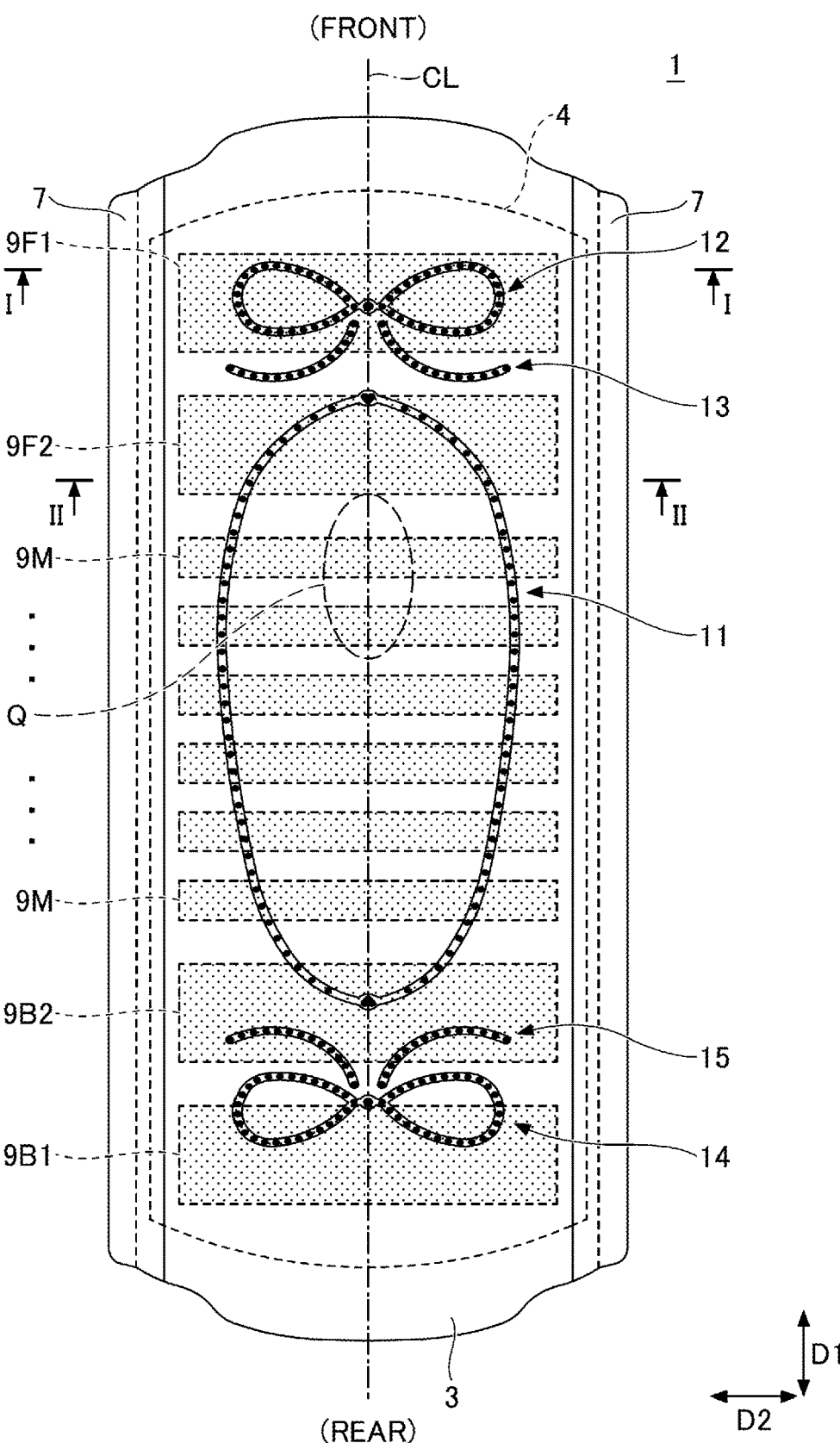
FIG. 1 is a plan view of an absorbent article according to an embodiment of the present disclosure as viewed from a skin side.

Hereinafter, an embodiment of the present disclosure will be described in detail with reference to the drawings. In the drawings, the same or corresponding components are denoted by the same reference numerals and the description thereof may be omitted unless otherwise specified.

(Basic Structure of Absorbent Article)

Figure 2:
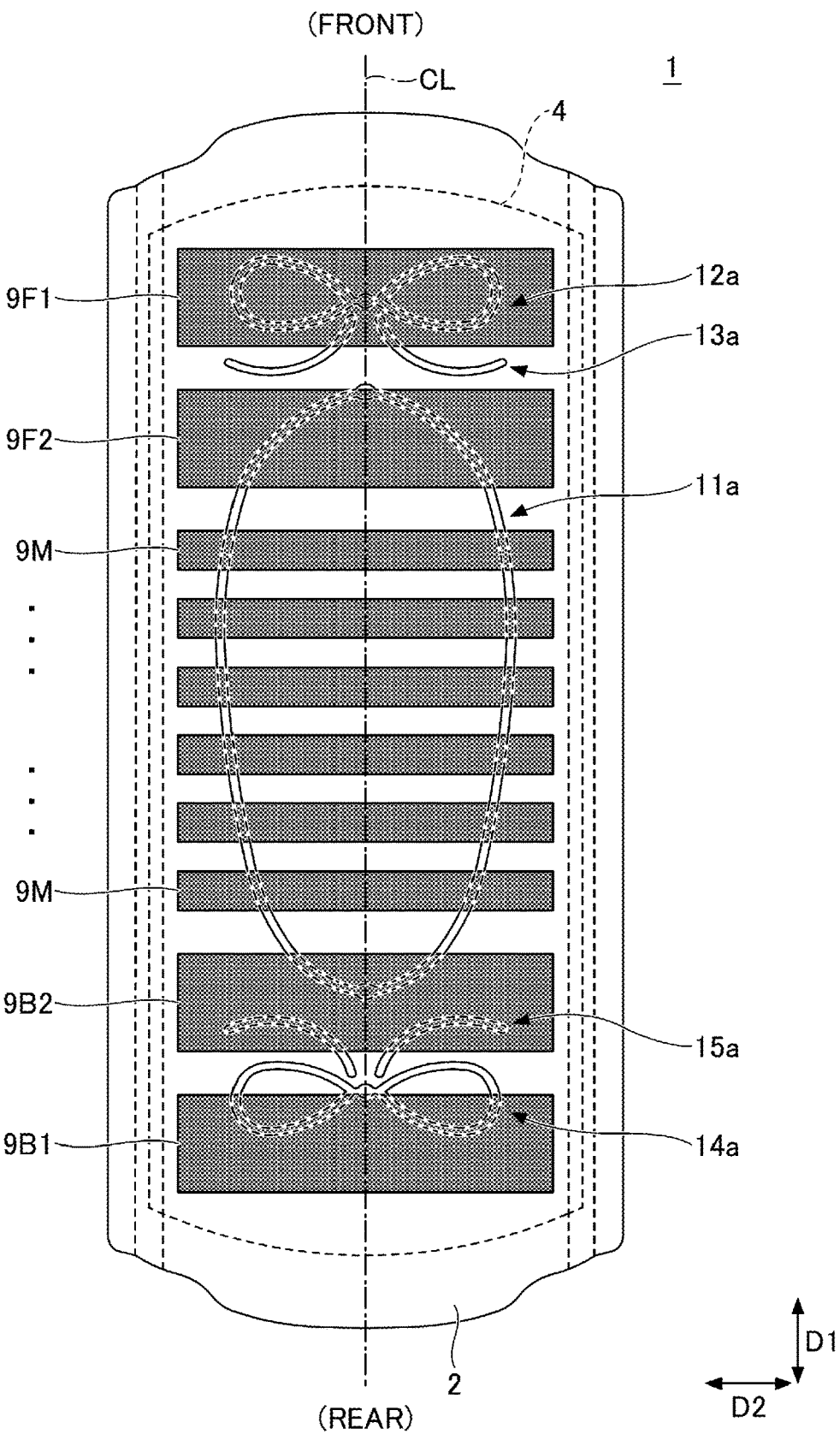
FIG. 2 is a plan view of the absorbent article according to the embodiment of the present disclosure as viewed from a non-skin side.
Figure 3:
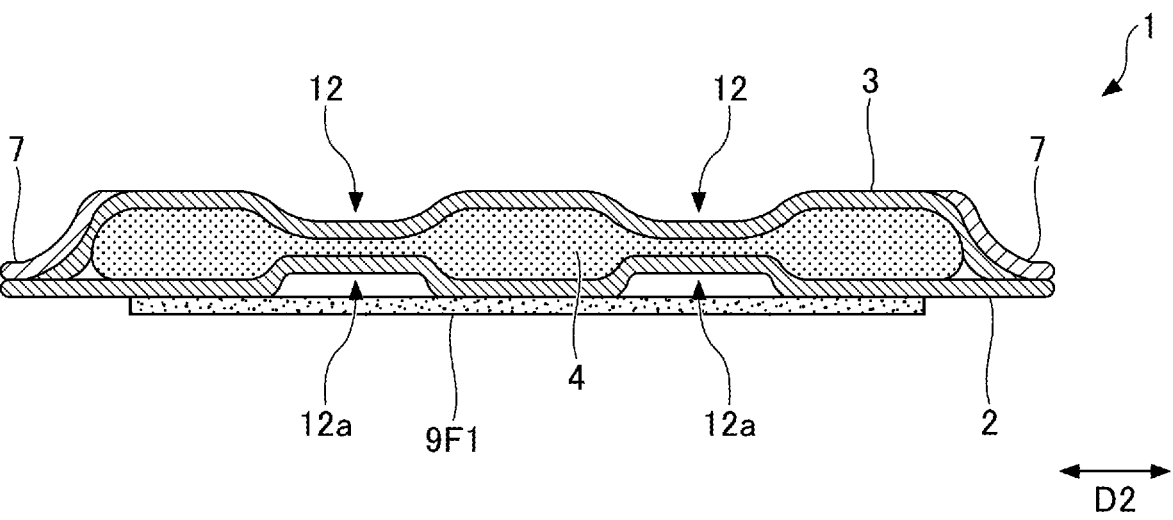
FIG. 3 is a cross-sectional view taken along line I-I of FIG. 1.
Figure 4:
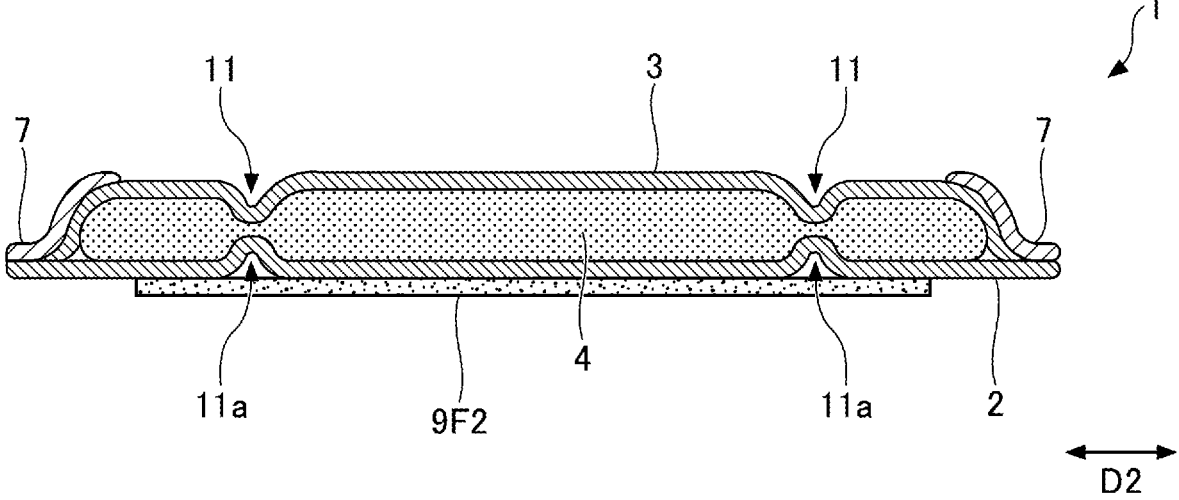
FIG. 4 is a cross-sectional view taken along line II-II of FIG. 1.

FIG. 1 shows a plan view of an absorbent article 1 according to an embodiment of the present disclosure as viewed from the skin side, that is, the side facing the wearer's skin when the absorbent article 1 is worn. FIG. 2 is a plan view of the absorbent article 1 viewed from the side opposite to that shown in FIG. 1, that is, the side facing underwear when worn (non-skin side). FIG. 3 is a schematic cross-sectional view taken along line I-I of FIG. 1, and FIG. 4 is a schematic cross-sectional view taken along line II-II of FIG. 1.

As shown in FIGS. 1 to 4, the absorbent article 1 may have a structure including a skin-side permeable top sheet, a non-skin-side impermeable back sheet 2, and an absorber 4 disposed between these sheets 2 and 3. Therefore, the absorbent article 1 has a flat pad shape.

Specifically, the absorbent article 1 may be a sanitary napkin, a panty liner (vaginal discharge sheet), a light incontinence pad, or the like, and is suitably used as a sanitary napkin. A sanitary napkin is described herein by way of example.

As shown in FIGS. 1 and 2, the absorbent article 1 may have a front-rear direction D1 along the front-rear direction of the wearer's body when worn, and a width direction D2 orthogonal to the front-rear direction D1. In the present embodiment, the absorbent article 1 has an elongated shape in the front-rear direction D1 in plan view, and the front-rear direction D1 of the absorbent article 1 is a longitudinal direction and the width direction D2 is a lateral direction. The total length of the absorbent article 1 (length in the front-rear direction D1) may be 140 to 420 mm. Further, the width of the absorbent article 1 (the length in the width-direction D2, and the length excluding wings or flaps extending from the side portions if there are any) can be set to 50 to 130 mm.

In the embodiment shown in FIG. 1, when a centerline (front-rear direction centerline) CL is drawn along the front-rear direction D1 in plan view, the absorbent article 1 has a substantially line-symmetric shape with the centerline as a line of symmetry, but the shape may not be line-symmetric. Further, configurations other than the shape of the absorbent article 1 (including the density and material of the absorber 4, the shape and size of the compressed groove, the shape and size of the displacement stopper, and the like) may also be substantially symmetrical with respect to the front-rear direction centerline CL as the axis of symmetry, or may be asymmetrical.

The back sheet 2 may be a sheet having at least water shielding properties, and may be, for example, a sheet made of an olefin resin such as polyethylene or polypropylene. It is also possible to use a polyethylene-sheet-laminated non-woven fabric or a nonwoven fabric layered sheet having a waterproof film interposed between the layers such that impermeability is substantially ensured. Further, it is preferable that a sheet material having moisture permeability is used to prevent stuffiness. As such a water shielding and moisture permeable sheet material, a microporous sheet can be used. The microporous sheet is obtained by forming a sheet by melting and kneading an inorganic filler with an olefin resin such as polyethylene or polypropylene, and stretching the sheet in a uniaxial direction or biaxial directions.

The top sheet 3 may be a sheet permeable to body fluids such as menstrual blood, vaginal discharge, urine and the like. Examples of suitable materials that may be used as the top sheet 3 include a porous or non-porous nonwoven fabric, a porous plastic sheet, and the like. Examples of material fibers constituting the nonwoven fabric include synthetic fibers such as olefin such as polyethylene or polypropylene, polyester and polyamide; regenerated fibers such as rayon or cuprammonium rayon; mixed fibers thereof; and natural fibers such as cotton. These fibers can be used alone or in combination with two or more kinds. Further, examples of a method for processing a nonwoven fabric include a spunlace method, a spunbond method, a thermal bond method, a melt blown method, and a needle punch method. Among the above methods, the spunlace method is preferred in terms of flexibility, the spunbond method is preferred because a nonwoven fabric with high drape properties can be manufactured, and the thermal bond method is preferred because a soft nonwoven fabric with high bulkiness can be manufactured. Furthermore, composite fibers including core-in-sheath fibers having a high-melting-point fiber as a core and a low-melting-point fiber as a sheath, side-by-side fibers, split fibers, and the like may be used, for example.

The absorber 4 is not particularly limited as long as it is a material capable of absorbing and retaining body fluids, but preferably includes cotton-like pulp and a water-absorbing polymer. Examples of the water-absorbing polymer that may be used include a superabsorbent polymer (SAP), a superabsorbent fiber (SAF), and a combination thereof. Examples of the pulp include cellulose fibers such as dissolving pulp, chemical pulp, and the like obtained from wood, and artificial cellulose fibers such as rayon, acetate, and the like. Softwood materials, hardwood materials, and the like may be used as the raw material for the chemical pulp, however, softwood materials are preferably used in view of their long fiber length and the like.

A synthetic fiber may be mixed into the absorber 4. Examples of the synthetic fiber that may be used include polyolefins such as polyethylene, polypropylene, and the like; polyesters such as polyethylene terephthalate, polybutylene terephthalate, and the like; polyamide such as nylon, and the like; and copolymers thereof. A combination of two or more of these materials may also be used. Further, composite fibers including core-in-sheath fibers having a high-melting-point fiber as a core and a low-melting-point fiber as a sheath, side-by-side fibers, split fibers, and the like may be used, for example. Hydrophobic fiber that has been surface-treated with a hydrophilizing agent to exabit affinity to body fluids may also be used, for example. The absorber 4 is preferably manufactured by a fiber stacking method or an air laid method.

The absorber 4 may be obtained by surrounding a main body portion thereof with an encapsulating sheet made of a crepe paper, a nonwoven fabric, or the like. Since the absorber 4 includes the encapsulating sheet, it is possible to prevent the absorber 4 from being twisted or split, and to maintain the shape. As the encapsulating sheet, an uncolored (that is, white) crepe paper or nonwoven fabric may be used, or a colored (for example, colored in a color like the color of the body fluid or a complementary color of the color of the body fluid) may be used. By using the colored encapsulating sheet, absorption of the body fluid by the absorber 4 can be made inconspicuous.

As shown in FIG. 1, the absorber 4 may have an elongated shape having a substantially constant width in plan view. Although the width of the absorber 4 may vary in the front-rear direction D1, the absorber 4 having a substantially constant width is preferable to avoid complicating the manufacturing apparatus. The absorber 4 may have a uniform thickness over the entire surface, but the thickness of the absorber 4 may not be uniform, and may be locally thin or thick. For example, it is possible to increase the thickness of a portion corresponding to body fluid discharge part Q which faces the body fluid discharge part of the wearer when the absorbent article is worn and the thickness of the periphery thereof, to form the absorbent article 1 to contact with the body of the wearer closer.

At both end portions of the absorber 4 in the front-rear direction D1, end portions of the back sheet 2 and the top sheet 3 may be bonded to each other with an adhesive, heat sealing, or the like. On both side portions of the absorbent article 1, that is, on both sides in the width direction D2, a pair of side sheets 7, 7 are disposed on the skin side (top sheet 3 side) in the front-rear direction D1.

The side sheet 7 may be formed by using a nonwoven fabric material subjected to an appropriate water-repellent treatment or a hydrophilic treatment in accordance with the purpose such as preventing permeation of body fluids or enhancing the touch feeling on the skin. The material of the side sheet 7 may be a natural fiber, a synthetic fiber, a regenerated fiber, or the like. When the side sheet 7 is subjected to a water-repellent treatment, a water-repellent agent such as a silicone-based agent or a paraffin-based agent can be used for the treatment. Note that the absorbent article may have a configuration in which the top sheet 3 extends to the end portion of the absorbent article 1 in the width direction D2 and is bonded to the back sheet 2 without using the side sheet 7.

Although the absorbent article 1 according to the illustrated embodiment is not provided with wings, the absorbent article 1 may have a pair of wings individually extending from each side portion near the portion corresponding to body fluid discharge part Q. The wing can be formed by bonding an extending portion of the side sheet 7 and an extending portion of the back sheet 2.

(Displacement Stopper)

As shown in FIGS. 1 to 4, on the back sheet 2 side of the absorbent article 1, there are formed displacement stoppers (9F1, 9F2, 9M, 9B1, 9B2) to reliably fix the absorbent article 1 to underwear for preventing displacement of the absorbent article 1 when worn. It is preferable that the displacement stopper is adhesive. The adhesive displacement stopper is formed, for example, by applying an adhesive that is a fluid material or by attaching a layer of an adhesive (adhesive tape or the like) formed in advance. As the adhesive used as the displacement stopper, a known adhesive, for example, a hot-melt type adhesive can be used. The major components thereof include styrene polymers, tackifiers, and plasticizers, as well as combinations thereof.

Examples of the styrene-based polymer include a styrene-ethylene-butylene-styrene block copolymer, a styrene-butylene-styrene block copolymer, a styrene-isobutylene-styrene copolymer, a styrene-butadiene-styrene block copolymer, and the like. These copolymers can be used alone or in combination of two or more kinds. As the tackifier and plasticizer, those which are solid at room temperature can be used. Examples of the tackifier include C5 oil resins, C9 oil resins, dicyclopentadiene oil resins, rosin-based oil resins, polyterpene resins, terpene phenol resins and the like. Examples of the plasticizer include monomer plasticizers such as tricresyl phosphate, dibutyl phthalate, and dioctyl phthalate, and polymer plasticizers such as vinyl polymers and polyesters.

As shown in FIGS. 1 and 2, a plurality of displacement stoppers is formed. The displacement stoppers individually extend in the width direction D2, and are spaced apart from each other in the front-rear direction D1. Each of the displacement stoppers has a length in the width direction D2 longer than a length in the front-rear direction D1. Such displacement stoppers disposed in the width direction D2 can prevent the displacement stoppers from being removed from the underwear when force is applied from both legs. In addition, since the plurality of displacement stoppers are provided so as to be separated from each other in the front-rear direction D1, even when the absorbent article 1 is curved in the front-rear direction D1 in accordance with the shape of the body at the time of wearing, it is possible to prevent the displacement stoppers from being unable to follow the curvature and from interfering with the curvature of the absorbent article 1.

The displacement stoppers may include the front displacement stoppers 9F1 and 9F2 formed forward of the absorbent article 1, the rear displacement stoppers 9B1 and 9B2 formed on the rear side thereof, and central displacement stoppers 9M, 9M, formed therebetween. In the example shown in FIGS. 1 and 2, the lengths of the plurality of displacement stoppers in the width direction D2 are the same, but the lengths of the front displacement stoppers 9F1 and 9F2 and the rear displacement stoppers 9B1 and 9B2 in the front-rear direction D1 are longer than the length of each of the central displacement stoppers 9M, 9M, . . . in the front-rear direction D1. As a result, the vicinity of the frontend portion and the rear end portion of the absorbent article 1 can be more reliably fixed to the underwear, and the flexibility of the central region of the article in the front-rear direction D1, which is largely curved when worn, can also be maintained.

The weight per unit area of the displacement stopper may be 20 to 50 gsm. The plurality of displacement stoppers may have the same weight per unit area or different weight per unit area. However, it is preferable that the weight per unit area within one displacement stopper is uniform to avoid complicating the manufacturing process.

(Non-Skin Side Groove)

In this embodiment, as shown in FIGS. 2 to 4, a groove recessed from the non-skin side to the skin side is formed in the absorbent article 1. The groove may be a portion where the absorber 4 alone or the absorber 4 and the back sheet 2 are recessed toward the skin side. That is, the groove recessed from the non-skin side to the skin side includes a state in which the absorber 4 is recessed and the back sheet 2 is recessed accordingly, and a state in which the back sheet 2 is placed substantially flat on the non-skin side of the absorber 4 but may be recessed in accordance with the recess of the absorber 4 when some force is applied. Such a groove may be formed in advance when the absorber 4 is laminated, or may be formed by compressing the absorber 4 alone, the absorber 4 and the back sheet 2 together, or the top sheet 3, the absorber 4, and the back sheet 2 together from the non-skin side. Further, the groove on the non-skin side may be formed by being distorted due to deformation of the skin side portion when the absorber 4 alone, the absorber 4 and the back sheet 2 together, or the top sheet 3, the absorber 4, and the back sheet 2 together are compressed from the skin side. In many absorbent articles, compressed grooves recessed from the skin side to the non-skin side are formed in the absorber 4 for promoting deformation along the body shape when worn and controlling the transfer of body fluids. Such compressed grooves on the skin side can be formed, for example, by placing the absorber 4 alone, a laminate including the top sheet 3 and the absorber 4, or a laminate including the top sheet 3, the absorber 4, and the back sheet 2 between a roll having protrusions corresponding to the shapes of the predetermined compressed grooves and a roll having no unevenness on the surface facing the roll such that the roll having the protrusions faces the skin side, and allowing the placed object to pass through therebetween.

As described above, the groove on the non-skin side in the present embodiment may be a groove formed on the non-skin side along with formation of a general compressed groove compressed from the skin side. In this case, the depth of the groove on the non-skin side is shallower than that of the compressed groove formed on the skin side (FIGS. 3 and 4).

As shown in FIG. 1, a plurality of compressed grooves is formed on the skin side. The number, shape, size, and placement of the compressed grooves are appropriately determined depending on the use of the absorbent article 1. In the example shown in FIG. 1, as the compressed groove, a central compressed groove 11 having a closed elliptical shape that is long in the front-rear direction D1 is formed at the center in the front-rear direction D1. Frontward of the central compressed groove 11, a first front compressed groove 12 close to the front end of the article, and second front compressed grooves 13 located rearward of the first front compressed groove 12 are formed. Rearward of the central compressed groove 11, a first rear compressed groove 14 close to the rear end of the article, and second rear compressed grooves 15 located frontward of the first rear compressed groove 14 may be formed. In the present embodiment, the first front compressed groove 12 and the first rear compressed groove 14 have a front-rear symmetrical shape, and the second front compressed grooves 13 and the second rear compressed grooves have a front-rear symmetrical shape. Further, the shape obtained by combining the first front compressed groove 12 and the second front compressed grooves 13 and the shape obtained by combining the first rear compressed groove 14 and the second rear compressed grooves 15 are symmetrical in the front-rear direction.

The first front compressed groove 12 is a continuous compressed groove. The first front compressed groove has a shape in which the up-down direction of the number 8 is turned sideways and arranged in the width direction D2 (or an infinite symbol) as a whole. In other words, it is a shape in which two ellipses arranged in the width direction D2 are joined at the center in the width direction D2. On the other hand, the second front compressed grooves 13 are constituted by a pair of compressed grooves spaced apart from each other in the width direction D2.

As shown in FIG. 1, the compressed groove may have a low compressed portion and a high compressed portion compressed more deeply than the low compressed portion. In FIG. 1, the low compression portion is shown in white and the high compression portion in black. As shown in FIG. 1, the high compression portion may be intermittently formed in the low compression portion.

As described above, by forming the skin-side compressed groove as shown in FIG. 1, a groove corresponding to the shape of the skin-side compressed groove is also formed on the non-skin side. Therefore, as shown in FIG. 2, a central groove 11a, a first front groove 12a, second front grooves 13a, a first rear groove 14a, and second rear grooves 15a having shapes corresponding to the central compressed groove 11, the first front compressed groove 12, the second front compressed grooves 13, the first rear compressed groove 14, and the second rear compressed grooves 15, respectively, are formed on the non-skin side of the absorbent article 1.

As shown in FIG. 2, the displacement stoppers are formed to overlap the grooves. In the illustrated example, each of the central groove 11a, the first front groove 12a, the second front grooves 13a, the first rear groove 14a, and the second rear grooves 15a is partially or entirely overlapped with any of the displacement stoppers.

Here, in a case where an adhesive displacement stopper is provided on the non-skin-side surface of the absorbent article 1 on which the groove is formed, the displacement stopper cannot partially or entirely come into contact with the groove portion, and a gap may be formed between the back sheet 2 and the displacement stopper. FIGS. 3 and 4 show a state in which gaps are formed between the first front groove 12a and the displacement stopper 9F1, and a state in which gaps are formed between the central compressed groove 11 and the displacement stopper 9F2, respectively, for the sake of explanation. However, the gap between the back sheet 2 and the displacement stopper may not be formed over the entire portion of the groove but a part thereof, or a very small part thereof. In that case, it can be such a state in which small air bubbles are enclosed between the back sheet 2 and the displacement stopper.

In this way, when the groove is formed on the non-skin side of the absorbent article 1, a portion in which the back sheet 2 and the displacement stopper are not in direct contact with each other is likely to occur therebetween. As a result, the adhesive force of the displacement stopper decreases. Therefore, in the case of the conventional absorbent article 1' including a non-skin-side groove 10a' and a displacement stopper 9' having no specific positional relationship according to the present embodiment (FIG. 5(a)), when the absorbent article 1' attached to underwear S at the time of wearing is to be removed from the underwear S, the displacement stopper 9' may be pulled toward the underwear side and tear at a position where the adhesive force between the underwear S and the displacement stopper 9' is larger than the adhesive force between a back sheet 2' and the displacement stopper 9'. A part of the displacement stopper may then remain on the underwear S as a displacement remaining piece r (FIG. 5(b)). In view of the fact that the direction in which the absorbent article 1 is removed is the front-rear direction D1 (for example, the direction from the front to rear), such a phenomenon (also referred to as an adhesive residue) is likely to occur when the displacement stopper overlaps a groove having a shape extending in the width direction D2 orthogonal to the front-rear direction D1 or a groove containing a large amount of component in the width direction D2.

The inventors of the present disclosure, however, have found that it is possible to prevent a displacement stopper from remaining on underwear (prevent an adhesive remaining phenomenon) by devising the arrangement of the displacement stopper with respect to a groove containing a large amount of component in the width direction D2 or a predetermined groove portion containing a large amount of component in the width direction D2 within the groove. That is, in the present embodiment, when the displacement stopper overlaps the groove on the non-skin side, the displacement stopper is arranged so that the groove portion containing a large amount of component in the width direction D2 is covered in the front-rear direction D1 in plan view. Accordingly, since the displacement stopper can be disposed in front of and back of the groove, the cohesive force of the material of the displacement stopper can be exerted from the front to the rear across the groove. Therefore, even if the adhesive force between the back sheet 2 and the displacement stopper is weakened at the position where the groove is formed, the portions of the displacement stopper portions not facing the groove in front of and back of the groove can pull the displacement stopper portion disposed facing the groove together by the cohesive force of the displacement stopper material, and the displacement stopper can be prevented from remaining on the underwear without being torn at the groove.

Figure 5:
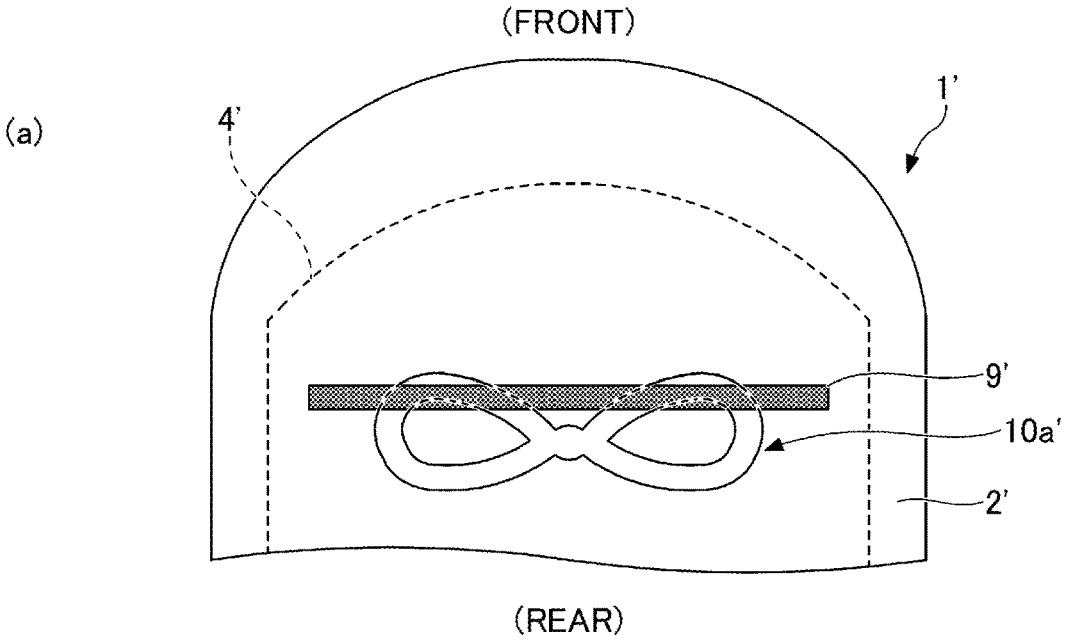
FIG. 5 is a diagram for explaining a conventional technique.
Figure 5:
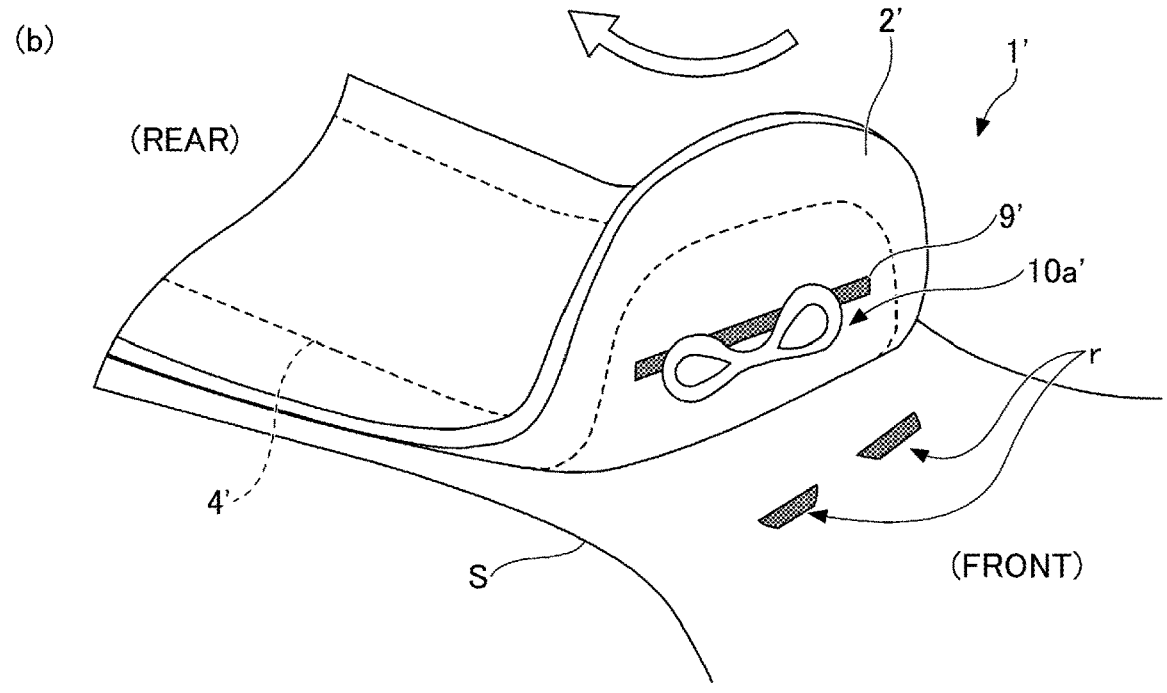
Figure 6:
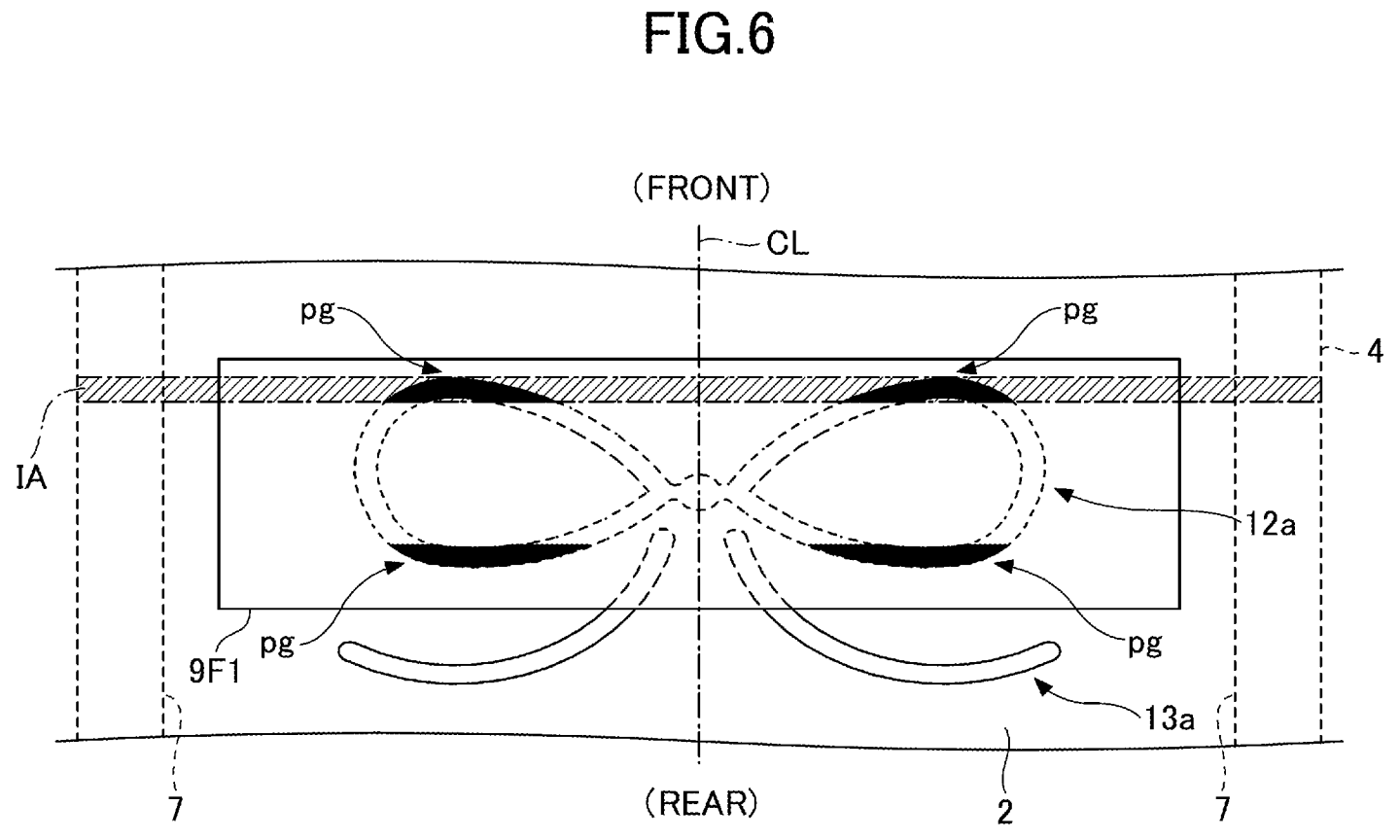

Here, the determination with respect to the groove portion will be described with reference to FIG. 6. FIG. 6 shows an enlarged view of a portion where the first front groove 12$a$ and the second front grooves 13$a$ are formed in FIG. 2. As described above, the first front groove 12$a$ forms a single continuous groove including two elliptical rings having a major axis in the width direction D2. That is, the continuous groove (first front groove 12$a$) has a shape having two or more portions protruding toward the front of the continuous groove and two or more portions protruding toward the rear of the continuous groove. In other words, the continuous groove may have a shape having two or more points at each of which a tangent line drawn at the outer edge of the continuous groove on the front side or the rear side thereof is parallel to the width direction D2. In the case where there is such a continuous groove having a shape having two or more portions protruding forward or backward, when the absorbent article 1 is removed from the underwear in the front-rear direction D1, two or more locations where the adhesive strength between the back sheet 2 and the displacement stopper becomes weak may occur at the same time or at close timings. In the case of the arrangement of the displacement stopper 9′ as shown in FIG. 5, since the displacement stopper 9′ is torn at two or more locations in the width direction D2, an adhesive residue is likely to occur. Therefore, a contrivance is required for the arrangement of the displacement stopper overlapping the continuous groove having such a shape having two or more portions protruding forward or backward.

The shape of the continuous groove is preferably bilaterally symmetrical (line-symmetrical with respect to the front-rear direction centerline CL as a line of symmetry). When there are two or more portions protruding forward, the front ends of those two or more protruding portions are preferably aligned in a line in the front-rear direction D1 (at the same line in the front-rear direction D1). Similarly, when there are two or more portions protruding rearward, it is preferable that the rear ends of those two or more protruding portions are aligned in a line in the front-rear direction D1 (at the same line in the front-rear direction D1).

Further, as shown in FIG. 6, in the continuous groove (first front groove 12$a$) having the above-mentioned specific shape, a portion, where an imaginary region IA overlaps the continuous groove 12$a$, the portion having an area of 3% or greater of the imaginary region IA, the portion not overlapping a centerline CL extending in the front-rear direction in plan view, the imaginary region IA having a unit length in the front-rear direction D1 and a same length in the width direction as the absorber, is defined as a predetermined groove portion pg. In FIG. 6, the predetermined groove Portions pg are shown in black. Note that the areas in which the imaginary region IA overlaps one continuous groove 12$a$ are preferably less than or equal to 30% of the whole area of the region from the viewpoint of ensuring the flexibility of the absorber 4. For example, in one continuous groove (for example, the first front groove 12$a$), when the rectangular imaginary area IA having a length in the front-rear direction D1 greater than or equal to the groove width of the continuous groove and having rectangular sides in the width direction D2 at sides of the absorber 4 in the width direction D2 is superposed on the continuous groove, if there may be the groove portions pg individually having an overlapping area with the imaginary region IA of greater than or equal to 3% relative to the area of the imaginary region IA, the displacement stopper 9F1 may be formed covering the groove portions pg in the front-rear direction D1 in plan view. However, any of the groove portions pg does not include the front-rear direction centerline CL in plan view. Further, the length of the groove portion pg in the width direction D2 may be longer than the groove width of the continuous groove, and may preferably be twice or more the groove width of the continuous groove.

The number of groove portions pg present in one continuous groove can be two or more as shown in FIG. 6, but may be one.

In the present embodiment, one displacement stopper is formed in a predetermined groove portion of a continuous groove so as to cover the groove portion in the front-rear direction D1. Furthermore, for example, as shown in FIG. 6, it is preferable that the displacement stopper 9F1 is formed covering the groove portions pg extending beyond forward and rearward the groove portions pg by a length of the groove portion pg of the groove 12$a$ in the front-rear direction D1 or a length greater than or equal to the groove width.

Thus, in front of and back of the predetermined groove portion pg, the displacement stopper extends in the front-rear direction D1 beyond the length of the groove portion pg in the front-rear direction D1, so that when the absorbent article 1 is removed from the underwear, for example, from the front to the rear, the displacement stopper portions not facing the groove in front of and back of the groove portion can pull the displacement stopper portion facing the groove, thereby further preventing the displacement stopper from remaining on the underwear. Here, a length of the displacement stopper extending forward from the front end of the groove portion pg or of that extending rearward from the rear end of the groove portion pg may be preferably 0.8 to 2.5 mm, more preferably 1.0 to 2.0 mm.

Furthermore, as shown in FIG. 6, the displacement stopper 9F1 that overlaps the entirety of the groove portions pg in the front-rear direction D1 overlaps the entirety of the continuous groove 12$a$ in the width direction D2. That is, when the displacement stopper 9F1 and the groove portions pg overlap each other, the continuous groove 12$a$ does not protrude from the displacement stopper 9F1 in the width direction D2 in plan view. As a result, the cohesive force of the displacement stopper material described above also acts in the width direction D2, and therefore, when the absorbent article 1 is removed from the underwear, it is possible to enhance the pulling force with respect to the displacement stopper portion which faces the predetermined groove portions pg and has a weak adhesive force to the back sheet 2.

In the example of FIG. 6, it can be said that the groove portions pg are portions of the continuous groove between a tangential line parallel to the width direction D2 at the front outer peripheral edge of the frontmost continuous groove in the absorbent article 1 and a tangential line parallel to the width direction D2 at the inner peripheral edge of the continuous groove. In addition, in the rearmost continuous groove in the absorbent article 1, the groove portions pg can be said to be portions of the continuous groove between a tangential line parallel to the width direction D2 at the rear outer peripheral edge of the rearmost continuous groove and a tangential line parallel to the width direction D2 at the inner peripheral edge of the continuous groove. With respect to such groove portions pg, it is preferable to provide the displacement stopper such that the maximum total length of the groove portions pg in the width direction D2 is more than or equal to 20% of the length in the width direction D2 of the displacement stopper that overlaps the continuous groove.

On the other hand, in the present embodiment, the displacement stopper may be formed so as not to overlap the predetermined groove portions pg in plan view. This is because if the displacement stopper does not overlap the groove portions pg in the first place, the problem of the displacement stopper remaining on the underwear (adhesive residue) does not occur. For example, the first rear groove 14a in FIG. 2 has a shape similar to that of the first front groove 12a, and the displacement stopper 9B1 is overlapped therewith. However, a side (front side) of the first rear groove 14a close to the center in the front-rear direction D1 does not overlap the displacement stopper 9B1.

Therefore, at the first rear groove 14a, there is no concern that the adhesive residue (FIG. 5(b)) may be generated in the predetermined groove portion pg on the side close to the center in the front-rear direction D1.

In the present embodiment, the relationship between the displacement stopper and the continuous groove on the non-skin side, in which one displacement stopper is provided so as to cover one continuous groove in the width direction D2 and the predetermined groove portions pg in the front-rear direction D1 in plan view, or does not overlap the groove portions pg, may be established in any region in the absorbent article 1, however, is preferably established in front of the absorbent article 1, particularly in front of the portion corresponding to body fluid discharge part Q. In other words, it is preferable that the above-described relationship, that is, the relationship in which one displacement stopper is provided so as to cover one continuous groove in the width direction D2 and the predetermined groove portions pg in the front-rear direction D1 in plan view, or does not overlap the groove portions pg, is established at least in the first front groove 12a in the example shown in FIG. 2. When the absorbent article 1 is removed from the underwear, many users remove the absorbent article from the front to rear, so that, in the removing operation, a strong force is likely to be suddenly applied at the front region, and there is a high possibility that the cohesive force of the displacement stopper is lost, and a part of the displacement stopper remains on the underwear. Therefore, since the continuous groove having the above-described predetermined arrangement relationship with the displacement stopper is formed on the front region, the above-described adhesive residue can be effectively avoided.

In order to prevent the displacement stopper from remaining on the underwear, it is conceivable to increase the weight per area of the adhesive displacement stopper or to widen the application range of the displacement stopper, for example, to apply the displacement stopper to the entire surface of the back sheet 2. By increasing the weight per area of the displacement stopper or by widening the application range of the displacement stopper, the cohesive force of the displacement stopper in the plane direction is improved, and the displacement stopper can be prevented from being torn. However, there is a possibility that increasing the weight per area of the displacement stopper increases the cost, or impairs the flexibility of the absorbent article to affect the wearing feeling. Therefore, according to the present embodiment, by forming the displacement stopper in a predetermined arrangement with respect to a continuous groove or not overlapping a Predetermined groove portion containing a large amount of component in the width direction D2, it is possible to avoid the adhesive residue without changing any of the weight per area or application range of the displacement stopper.

The length of one displacement stopper in the front-rear direction D1 depends on the length of the predetermined groove portion pg of the continuous groove in the front-rear direction D1, but is preferably 7 to 50 mm. By setting the length of the displacement stopper in the front-rear direction D1 to be in the above-described range, it is possible to maintain the flexibility of the absorbent article 1 while achieving the above-described effect of avoiding the adhesive residue.

(Modified Example of Absorbent Article)

Figure 7:
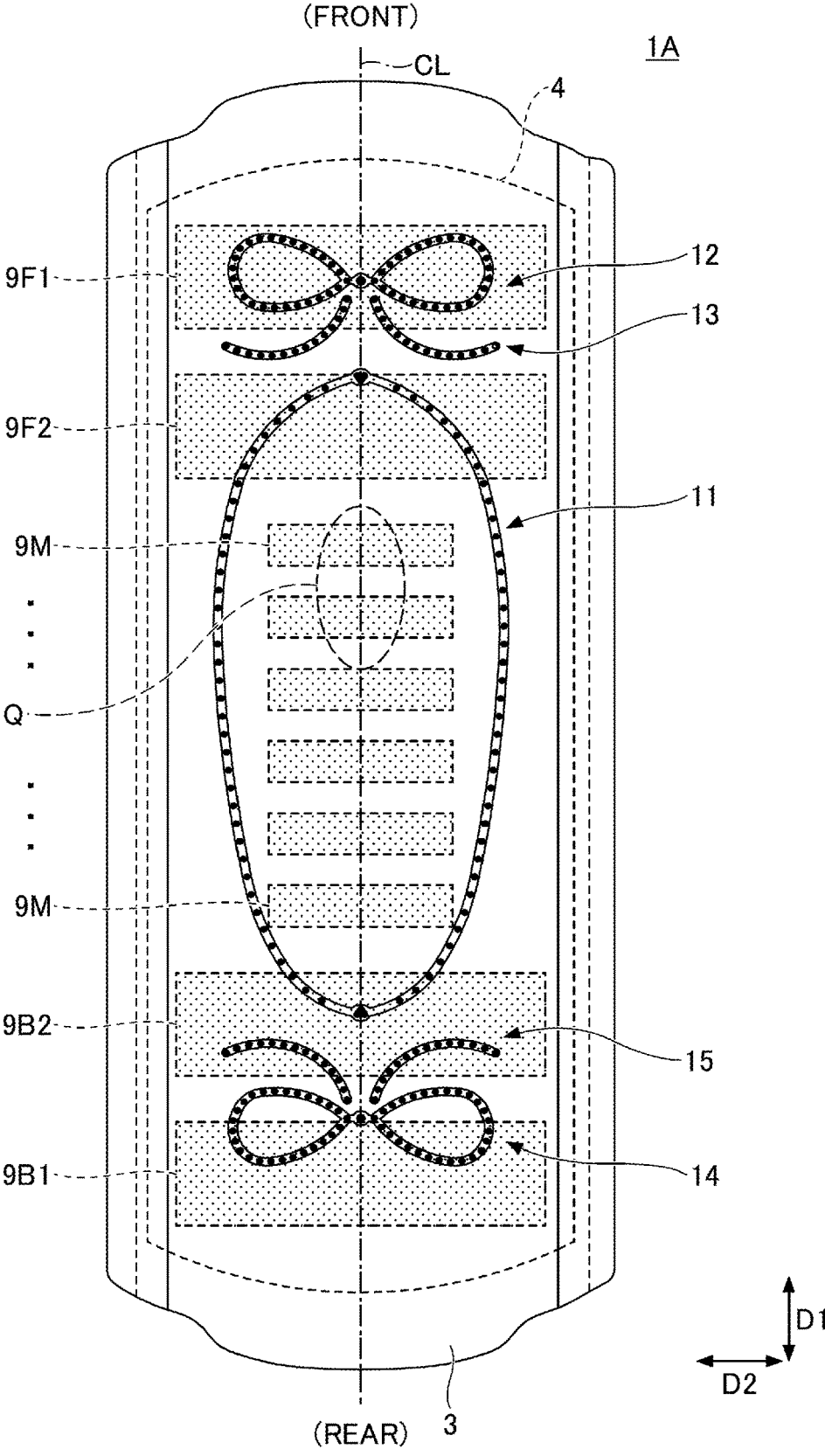
FIG. 7 is a plan view of an absorbent article according to a modified example as viewed from the skin side.

FIG. 7 shows a plan view of an absorbent article 1A according to a modified example when viewed from the skin side. The configuration of the absorbent article 1A is basically the same as that of the absorbent article 1 (FIG. 1), but is different from the absorbent article 1 in terms of the size of the absorbent article and the arrangement of the displacement stoppers in the central region in the front-rear direction D1. The absorbent article 1A is slightly longer than the absorbent article 1. Further, in the absorbent article 1A, the front displacement stoppers 9F1 and 9F2 and the rear displacement stoppers 9B1 and 9B2 are arranged in the same manner as those of the absorbent article 1, but each length of the central displacement stoppers 9M, 9M, . . . in the width direction D2 is shorter than that of the front displacement stoppers 9F1 and 9F2 and that of the rear displacement stoppers 9B1 and 9B2. Therefore, this example is preferable in that flexibility is high in the central region of the front-rear direction D1.

Furthermore, in the absorbent article 1A, the central displacement stoppers 9M, 9M, are disposed so as not to overlap the central compressed groove 11 in plan view, and not to overlap the central groove (not shown) on the non-skin side. Therefore, in this example, in addition to the effect obtained by the absorbent article 1 (FIG. 1), the displacement stoppers are less likely to remain on the underwear even in the vicinity of the region where the central compressed groove 11 is formed.

<About Manufacture>

The method for providing the displacement stopper on the back sheet 2 is not particularly limited, but the displacement stopper can be provided by applying a liquid adhesive using a coating device such as a gravure coater, a spray coater, a spiral gun, or a bead gun. The displacement stopper extending in the width direction D2 can be formed by applying an adhesive discharged from the positionally fixed coating device to the absorbent article 1 conveyed in the width direction D2 of the absorbent article 1 by a conveyor such as a belt conveyor.

Instead of applying an adhesive to the back sheet 2, an adhesive may be applied to a packaging sheet or a release sheet to be opposed to the back sheet 2 at the time of individual packaging, and then the back sheet 2 of the absorbent article 1 may be placed to be opposed to the packaging sheet or the release sheet. Here, once the packaging sheet or the release sheet is subjected to release treatment, the adhesive is transferred to the back sheet 2 of the absorbent article 1 when the absorbent article 1 is removed from the packaging sheet or the release sheet at the time of use, and can therefore function as a displacement stopper.

Further, when the adhesive is applied to the release sheet, only the back sheet 2 is superposed on the release sheet to which the adhesive is applied, and thereafter, a laminate of the absorber 4 formed with the compressed grooves and the top sheet 3 is placed thereon to complete the absorbent article 1. In this case, even if the laminate of the absorber 4 and the top sheet 3 is pressed from the skin side, a gap is less likely to be formed between the displacement stopper and the back sheet 2, which is preferable.

Hereinafter, specific embodiments of the present disclosure will be described.

(Appended Clause 1)

An embodiment according to Appended Clause 1 provides an absorbent article including a skin-side permeable top sheet, a non-skin-side impermeable back sheet, and an absorber disposed between the top sheet and the back sheet, the absorbent article having a front-rear direction corresponding to a front-rear direction of a body of a wearer and a width direction orthogonal to the front-rear direction, wherein the absorber has at least one continuous groove recessed from a non-skin side to a skin side, wherein the back sheet is provided on a non-skin side with a plurality of adhesive displacement stoppers, each having a length in the width direction longer than a length in the front-rear direction, at intervals in the front-rear direction, for fixing the absorbent article to underwear, wherein the continuous groove has a shape having two or more portions protruding toward a front of the continuous groove and/or having two or more portions protruding toward a rear of the continuous groove, wherein the continuous groove includes a groove portion, where an imaginary region overlaps the continuous groove, the groove portion having an area of 3% or greater of the imaginary region, the groove portion not overlapping a centerline extending in the front-rear direction in plan view, the imaginary region having both a unit length in the front-rear direction and a same length in the width direction as the absorber, and wherein the displacement stopper overlaps an entirety of the continuous groove in the width direction and an entirety of the groove portion in the front-rear direction, or does not overlap the groove portion, in plan view.

In the embodiment according to Appended Clause 1, even if the continuous groove appearing on the non-skin side (back sheet side) of the absorbent article has a predetermined groove portion having two or more portions protruding toward the front of the continuous groove and/or having two or more portions protruding toward the rear of the continuous groove and containing a large amount of component in the width direction, it is possible to prevent or reduce the adhesive displacement stopper from remaining on the underwear by overlapping the displacement stopper in a predetermined arrangement with respect to the groove portion in plan view, or by not overlapping the displacement stopper with the groove portion in plan view.

In the former case where the displacement stopper overlaps the predetermined groove portion, the displacement stopper extends including the continuous groove in the width direction and the groove portion in the front-rear direction in plan view. For this reason, since the displacement stopper is also disposed in front of and in back of the groove portion of the continuous groove, the cohesive force of the displacement stopper material can be exerted in the front-rear direction across the groove portion. Therefore, when the absorbent article is removed from the underwear in the front-rear direction (for example, from the front to the rear), even if the adhesion between the displacement stopper portion facing the groove portion as a part of the continuous groove and the back sheet is weakened, the displacement stopper portions disposed facing the front and rear portions of the groove portion (portions where no groove is formed) and maintaining the adhesion with the back sheet can pull the displacement stopper portion disposed facing the predetermined groove portion. Therefore, it is possible to reduce the possibility or avoid that the displacement stopper is transferred from the back sheet to the underwear in the groove portion. In addition, since the displacement stopper is provided covering the continuous groove in the width direction, the cohesive force of the displacement stopper easily acts also in the width direction, and it is possible to prevent the displacement stopper from being torn at a position facing the continuous groove and remaining on the underwear.

Further, in the latter case where the displacement stopper does not overlap the predetermined groove portion, since the displacement stopper does not face the groove portion in the first place, there is no concern that the displacement stopper is transferred from the back sheet to the underwear.

(Appended Clause 2)

In an aspect according to Appended Clause 2, the displacement stopper covers the entire continuous groove in plan view.

According to the aspect of Appended Clause 2, since the displacement stopper covers the entire continuous groove in plan view, it is possible to extend a region not facing the groove around the predetermined groove portion. Since the cohesive force of the displacement stopper material acts because the displacement stoppers are continuous in the surface direction, the above configuration allows the cohesive force of the displacement stopper material to act over a wider range. Therefore, when the absorbent article is removed from the underwear, it is possible to further prevent the displacement stopper from being torn at the position of the predetermined groove portion and being transferred to the underwear.

(Appended Clause 3)

In an aspect according to Appended Clause 3, the displacement stopper has a length in the front-rear direction of 7 to 50 mm.

According to the aspect of Appended Clause 3, since the displacement stopper has a predetermined length in the front-rear direction, the effect of the displacement stopper portions not facing the continuous groove that are present in front of and back of the continuous groove pulling the displacement stopper portion facing the continuous groove is improved, and the possibility of the flexibility of the absorbent article being impaired can be reduced without the displacement stopper being too long in the front-rear direction.

(Appended Clause 4)

In an aspect according to Appended Clause 4, the displacement stopper extends beyond the groove portion forward and rearward by a length more than or equal to the length of the groove portion in the front-rear direction.

According to the aspect of Appended Clause 4, the displacement stopper portions disposed in front and back of the predetermined groove portion can pull the displacement stopper portion facing the groove portion, and the effect of preventing the displacement stopper from remaining on the underwear can be further enhanced.

(Appended Clause 5)

In an aspect according to Appended Clause 5, the continuous groove has a shape corresponding to a compressed groove formed on the skin side.

According to the aspect of Appended Clause 5, since the continuous groove is a groove generated on the non-skin side corresponding to the shape of the compressed groove along with the formation of the compressed groove (fit emboss) on the skin side of the absorbent article, the depth of the continuous groove is suppressed to be shallow. Even if the case of such a shallow groove, when the displacement stopper is disposed on the non-skin side of the absorbent article, air bubbles are trapped or the like, and a gap may be generated between the back sheet and the displacement stopper. However, by providing the displacement stopper in a predetermined arrangement as described above in the aspect according to Appended Clause 1, it is possible to prevent the displacement stopper from remaining on the underwear. Since many absorbent articles are formed with compressed grooves on the skin side, this aspect can address the problem of the displacement stoppers remaining on the underwear for many absorbent articles.

(Appended Clause 6)

In an aspect according to Appended Clause 6, the absorbent article has a portion corresponding to a body fluid discharge part that faces a body fluid discharge part of a wearer, and the continuous groove is formed at least forward of the portion corresponding to the body fluid discharge part.

When the absorbent article is removed from the underwear, many users hold the front part of the absorbent article and remove backward.

Therefore, a removing operation at the front part is likely to be a sudden operation because it is the start of the removal operation, and the displacement stopper is likely to remain on the underwear. According to the aspect of Appended Clause 6, since at least the continuous groove and the displacement stopper disposed in front thereof have the positional relationship according to Appended Clause 1, the effect of this aspect is more effectively exhibited.

This application claims priority to Japanese Patent Application No. 2021-158364 filed on Sep. 28, 2021 with the Japan Patent Office, the entire contents of which are incorporated herein by reference.

LIST OF REFERENCE NUMERALS 1, 1A Absorbent article
2 Back sheet
3 Top sheet
4 Absorber
7 Side sheet
9, 9F1, 9F2, 9B1, 9B2, 9M
10 Adhesive displacement stopper
11 Central compressed groove
12 First front compressed groove
13 Second front compressed groove
14 First rear compressed groove
15 Second rear compressed groove
11a Central groove
12a First front groove
13a Second front groove
14a First rear groove
15a Second rear groove
D1 Front-rear direction
D2 Width direction
pg Predetermined groove portion in continuous groove
Q Portion corresponding to body fluid discharge part

The invention claimed is:

1. An absorbent article comprising a skin-side permeable top sheet, a non-skin-side impermeable back sheet, and an absorber disposed between the top sheet and the back sheet, the absorbent article having a front-rear direction configured to correspond to a front-rear direction of a body of a wearer and a width direction orthogonal to the front-rear direction, wherein the absorber has at least one compressed groove recessed from a skin side to a non-skin side and at least one continuous groove recessed from the non-skin side to the skin side such that a shape recessed from the non-skin side to the skin side of the at least one continuous groove corresponds to a shape recessed from the skin side to the non-skin side of the at least one compressed groove, each shape recessed from the non-skin side to the skin side of the at least one continuous groove being formed with a contour that is substantially the same as the contour of an entire shape recessed from the skin side to the non-skin side of the at least one compressed groove, wherein the back sheet is provided on a non-skin side with a plurality of adhesive displacement stoppers, each having a length in the width direction longer than a length in the front-rear direction, at intervals in the front-rear direction, for fixing the absorbent article to underwear, wherein the continuous groove extends across a centerline extending in the front-rear direction, extending more than half of a width of the absorber in the width direction, and has a shape having two or more portions protruding toward a front of the continuous groove and/or having two or more portions protruding toward a rear of the continuous groove, wherein the continuous groove has a groove portion, where an imaginary region overlaps the continuous groove, that has an area of 3% or greater of the imaginary region and that does not include the centerline extending in the front-rear direction in plan view, the imaginary region defined by both a unit length overlapping the continuous groove in the front-rear direction and a same length in the width direction as the absorber, wherein at least one displacement stopper of the plurality of adhesive displacement stoppers at least partially overlaps the continuous groove in the width direction and the groove portion in the front-rear direction in plan view, wherein the imaginary region has, in plan view, a rectangular shape having two opposite sides having a first length and two different opposite sides having a second length, the first length being equal to a maximum width of the absorber in the width direction, the second length being a same groove width of the continuous groove in the front-rear direction, and wherein a predetermined area of the imaginary region that is overlapped by the continuous groove is less than or equal to 30% of a whole area of the imaginary region defined by the rectangular shape in plan view.

2. The absorbent article according to claim 1, wherein the at least one displacement stopper includes an entirety of the continuous groove in plan view.

3. The absorbent article according to claim 1, wherein the at least one displacement stopper has a length of 7 to 50 mm in the front-rear direction.

4. The absorbent article according to claim 1, wherein the at least one displacement stopper extends beyond the groove portion forward or rearward by a length more than or equal to a length of the groove portion in the front-rear direction.

5. The absorbent article according to claim 1, further including a portion configured to correspond to a body fluid discharge part which is configured to face the body fluid discharge part of the wearer, wherein the continuous groove is formed at least forward of the portion configured to correspond to the body fluid discharge part.

* * * * *